United States Patent [19]

Lamb et al.

[11] Patent Number: 4,804,000
[45] Date of Patent: Feb. 14, 1989

[54] DYNAMIC SAGITTAL KNEE TEST APPARATUS

[76] Inventors: Steve Lamb, 6724 Corte Del Vista, Pleasanton, Calif. 94545; Larry W. Lamoreux, 5470 Manila Ave., Oakland, Calif. 94618

[21] Appl. No.: 5,921

[22] Filed: Jan. 21, 1987

[51] Int. Cl.$^4$ .............................................. A61B 5/10
[52] U.S. Cl. ...................................... 128/774; 33/512
[58] Field of Search ................ 128/774, 782; 73/379; 33/511, 512

[56] References Cited

U.S. PATENT DOCUMENTS

| | | | |
|---|---|---|---|
| 4,306,571 | 12/1981 | McLeod, Jr. | 128/782 |
| 4,436,099 | 3/1984 | Raftopoulos | 128/782 |
| 4,534,364 | 8/1985 | Lamoreux | 128/774 |

FOREIGN PATENT DOCUMENTS 1175434  8/1985  U.S.S.R. ............................. 128/774

Primary Examiner—Edward M. Coven
Assistant Examiner—Randy Citrin
Attorney, Agent, or Firm—Bielen and Peterson

[57] ABSTRACT

Apparatus for electronically measuring ligamentous insufficiencies in the knee, the apparatus constructed in an exoskeletal articulating framework that is secured above the knee to the patient's femur and below the knee to the tibia and has substantially skeletal conforming articulating joint members with measuring means for determining the relative motions of tibia to femur.

20 Claims, 3 Drawing Sheets

Microfiche Appendix Included
(1 Microfiche, 78 Pages)

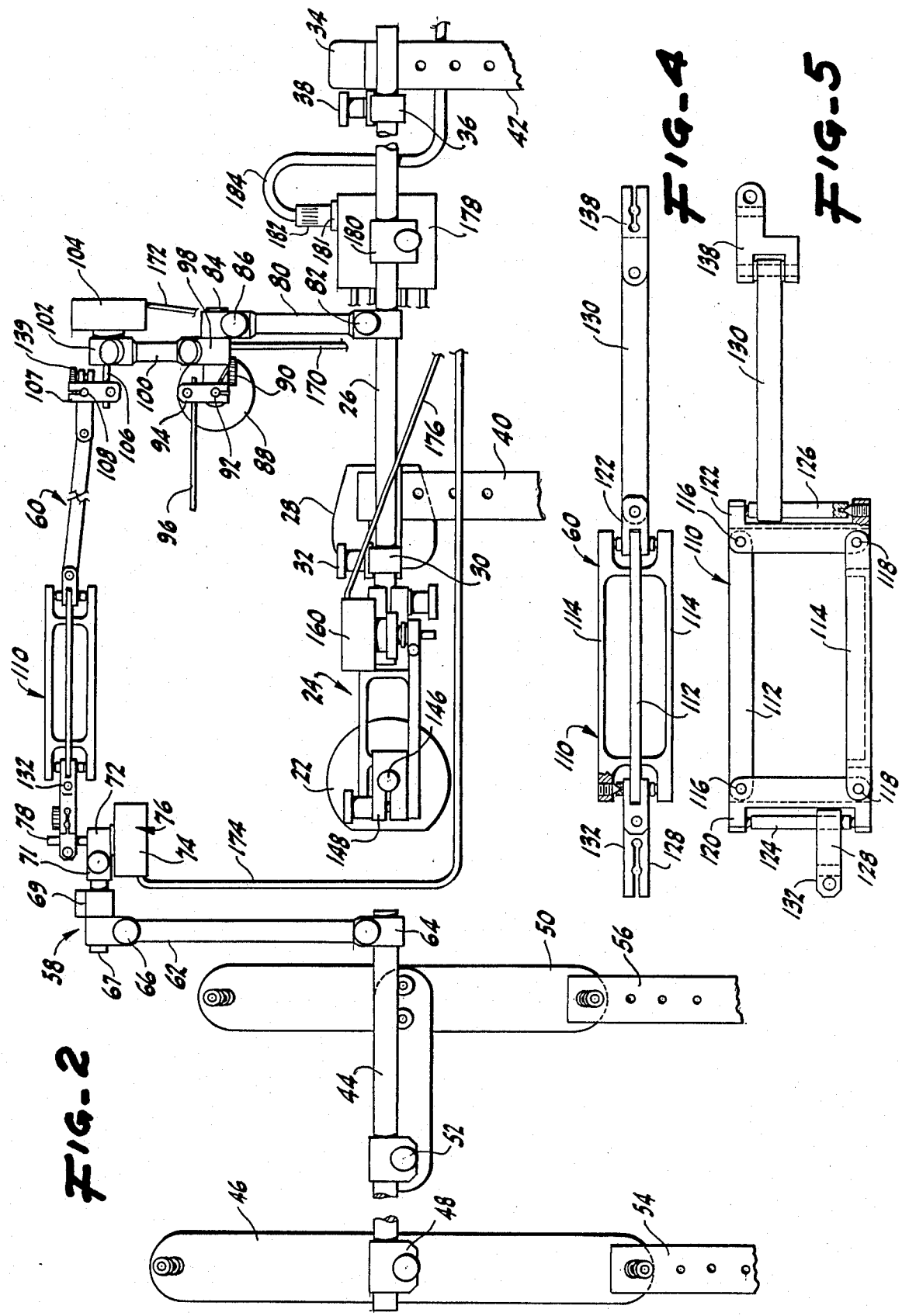

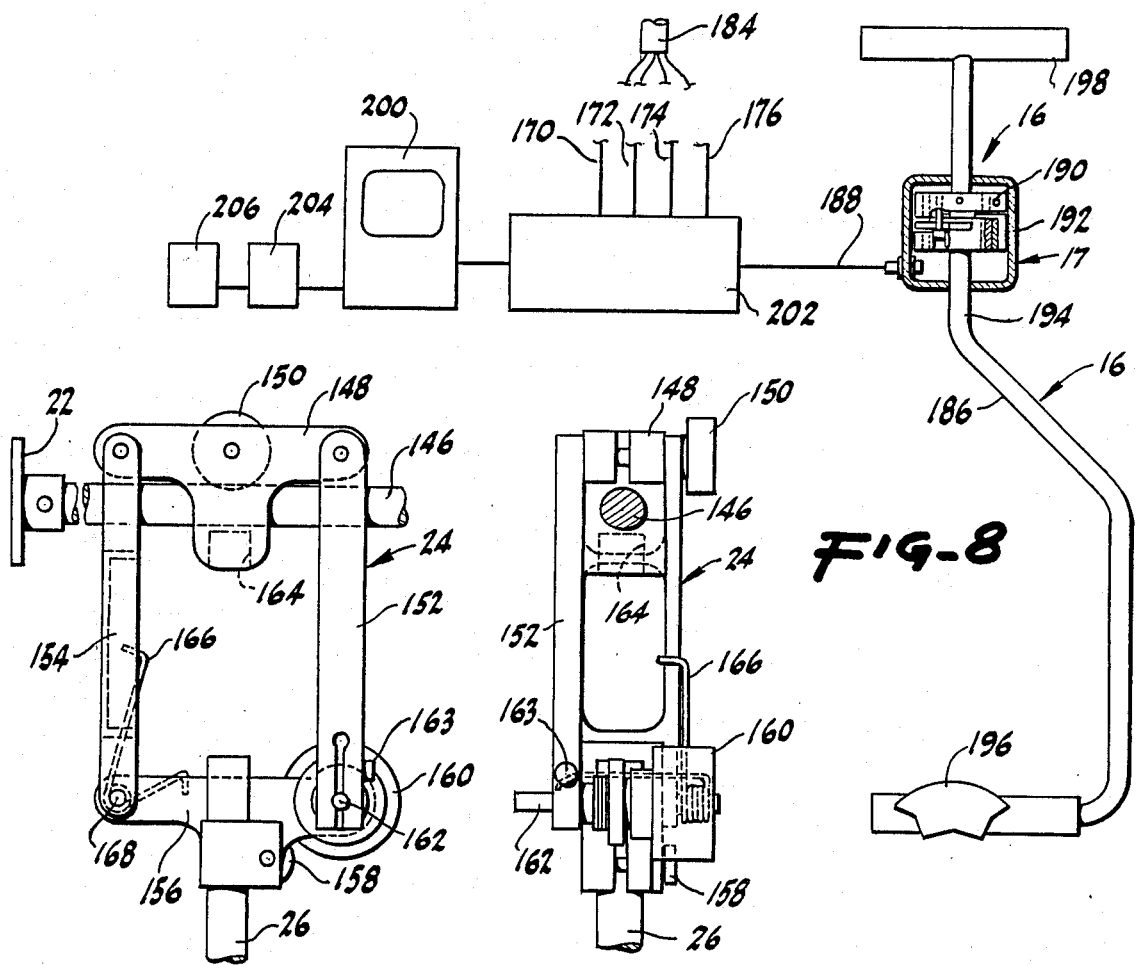
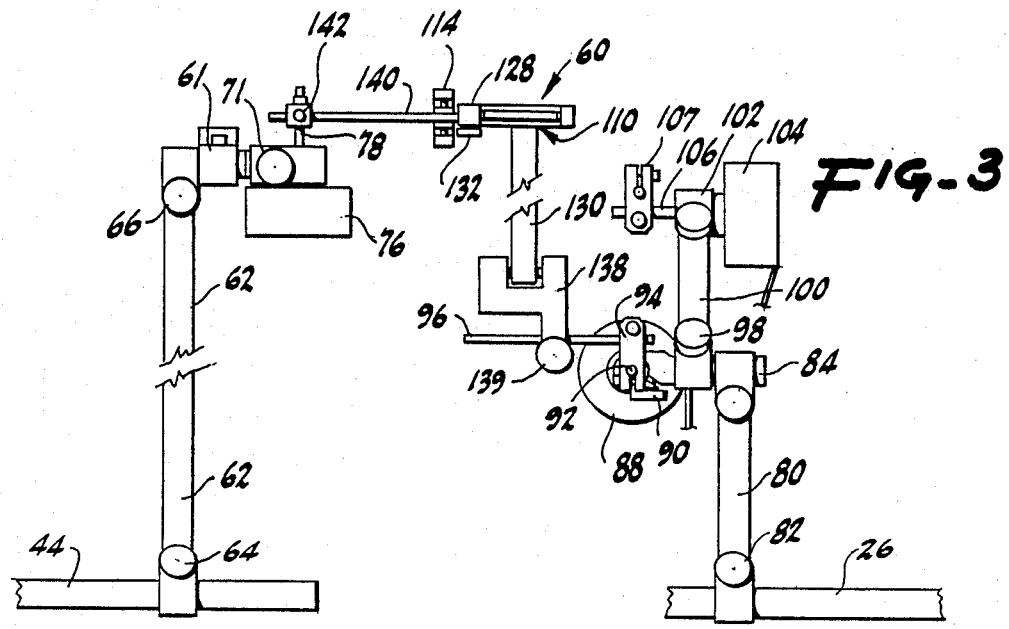

DYNAMIC SAGITTAL KNEE TEST APPARATUS

BACKGROUND OF THE INVENTION

A microfiche appendix consisting of one sheet with seventy-eight frames is available.

This invention relates to apparatus for measuring ligamentous insufficiency in the knee to enable a physician to provide a diagnosis of injury or abnormal operation for evaluation of different treatment methods. In the past, abnormal motion between the tibia and the femur was detected by a physician by manipulation of the leg by hand. Often the motion of a leg with a ligament tear is subtle and difficult to quantify or even compare with the patient's uninjured leg. Because a normal knee may have a substantial motion, it is desirable to quantitatively measure the displacement to allow an accurate comparison between the patient's normal and injured knees to determine the extent of injury. Further, it is desirable to quantify such measurements to compare motion of the patient's knee with statistical norms or with past records to monitor the progress of treatment.

While an electromechanical instrument has been devised for measuring the anterior drawer in the legs of normal volunteers and patients with known anterior cruciate deficits in a clinical research study, the device has certain disadvantages. The instrument is expensive and bulky and is not autoclavable to allow for its use in the operating room. Further, the instrument cannot measure knee motions of the knee when the patient is standing or walking.

The apparatus of this invention is autoclavable and is designed for use in both the 20° anterior draw and 90° anterior draw tests and without refitting is designed for use in measuring posterior excursions. It is believed that measurement of both anterior and posterior excursions provides the physician with the maximum useful data for proper diagnosis and treatment.

The first of such instruments utilized a modified dental chair and measurements of knee laxity were obtained by measuring motion relative to the chair. This required that the patient's leg be immobilized at various points to assure accuracy of the measurements. Improved devices, such as that disclosed in our U.S. Pat. No. 4,534,364, issued Aug. 13, 1985, entitled, "Sagittal Knee Test Apparatus," provide exoskeletal frame structures that permit comparative measurements to be taken from the light weight frame structure itself, thus freeing the patient from the chair and improving the accuracy of measurements. Such apparatus was nevertheless designed for operation while a patient was seated, preferably with an adjustable support device for the lower legs as described in the cited reference. While the improved device described was mechanical in operation, other devices for anterior/posterior laxity measurement have utilized electronic, leg mounted measuring means in conjunction with leg supports of various types.

In addition to anterior/posterior laxity measurement, it is advantageous to measure varus-valgus laxity and axial rotation of the tibia relative to the femur. These additional measurements greatly enhance the ability to correctly determine the severity of injury and in particular whether it is the anterior cruciate ligament, medial collateral ligament or both that are damaged.

In designing equipment for measuring knee laxities it is desirable to have the measuring framework connect to the body at long skeletal prominences with minimal restriction of normal joint motions. The framework must therefore be light in weight and mechanically self-contained without mechanical connection to external structures. Preferably, the exoskeletal structure should permit ambulatory motion to allow measurements to be obtained during normal movement such as walking as well as during conventional, contrived examination procedures. Although such an ambulatory exoskeletal framework has been experimentally constructed for hip motions including tibial rotations, heretofore such a structure adapted to measure anterior/posterior and varus-valgus laxities as well as tibial rotation has not been devised. The dynamic sagittal knee testor of this invention is designed to perform the standard knee laxity tests at various measured flexion angles of the lower leg and uniquely generate laxity measurements while walking.

SUMMARY OF THE INVENTION

The dynamic sagittal knee test apparatus of this invention relates to those devices used to measure laxity or deficiencies in the knee, usually to diagnose injuries often resulting from sports where the foot is immobilized and dynamic forces are applied to the leg or knee as in cleat sports and skiing. Laxity measuring instruments have become sufficiently sensitive that more subtle deficiencies in the knee than major ligament tears are detectable.

The dynamic knee test apparatus of this invention is a light weight, exoskeletal frame that is attached to the user's upper and lower leg and is used in conjunction with an adjustable leg support seat as described in our referenced patent or without such seat with the patient standing or walking. Other devices do not have this versatility which permits measurements to be taken when the patient applies his natural weight to the knee as well as external forces. In addition to the conventional anterior/posterior laxity measurements to which conventional portable knee test apparatus is limited, the apparatus of the invention measures varus-valgus laxity and axial rotation of the tibia while recording the flexion angle of the leg.

The measurements are electronically taken and coordinated by a personal computer using a software program for instantaneous display on a monitor. Permanent records may be obtained using conventional accessory printers.

In construction, the knee test apparatus attaches a light weight tubular reference element to each skeletal segment of interest and then measures relative motions between the reference elements by linking structures and displacement sensing transducers. Thus, in the preferred embodiment a first elongated, tubular element is mounted to the thigh on a pair of displaced mounting pads strapped to the upper and lower thigh such that the tubular rod is aligned with the femur. While the thigh lacks the body prominences preferred for detecting subtle motions of the exoskeleton, the femur element is the reference element, and visual alignment with secure strapping is sufficient for the rod to maintain its position with respect to the femur during translocations of the tibia.

A second elongated, light-weight, tubular element is mounted to the tibia on a pair of displaced mounting pads seated on bony prominences such that the tubular rod parallels all movements of the tibia. Interconnecting the femoral rod and the tibial rod is a side linkage with a first radial transducer positioned at the axis of overall knee flexion to detect the relative angle of tibia and femur and alternate second and third radial transducers to selectively detect axial rotation or varus-valgus motions respectively. The former motion is of the type induced by twisting the foot and the latter by side forces on the lower leg with the knee immobilized. Data obtained from measurement of these motions is particularly useful in determining exactly which ligament in the knee is damaged or severed and often where it is damaged.

The standard anterior/posterior laxity measurements are taken by a fourth transducer connected to the support linkage of a floating patella pad positioned at the end of the tibial rod in contact with the patella. The patella pad is proximate the upper support pad which contacts the bony tibial tubercle. Since the patella follows the femur, subtle fore and aft displacements of the tibia relative to the femur are accurately represented by displacements of the patella pad and tibial tubercle contact pad. A small spring in the patella pad linkage biases the pad against the patella such that measurements can be taken while the patient is standing or walking.

Signals from the sensors are sent to a processor where the radial detections are translated, in most cases, to equivalent angular displacements which may be represented on conventional gauges or digital displays. Preferably the signals are sent to a computer processor where various two dimensional displays graphically depict various motions as desired by the diagnostician.

BRIEF DESCRIPTION OF THE DRAWINGS

FIG. 2 is a top assembly view partially fragmented of the test apparatus of FIG. 1 in an extended position.

FIG. 3 is a partial top assembly view of the test apparatus of FIG. 2 in an alternate connection configuration.

FIG. 4 is a top view of a spanning linkage assembly.

FIG. 5 is a side view of the assembly of FIG. 4.

FIG. 6 is a side view of a patella pad linkage assembly.

FIG. 7 is an end view of the assembly of FIG. 6.

FIG. 8 is a side elevational view of a force applicator in schematic conjunction with a computer.

DETAILED DESCRIPTION OF THE PREFERRED EMBODIMENT

Figure 1:
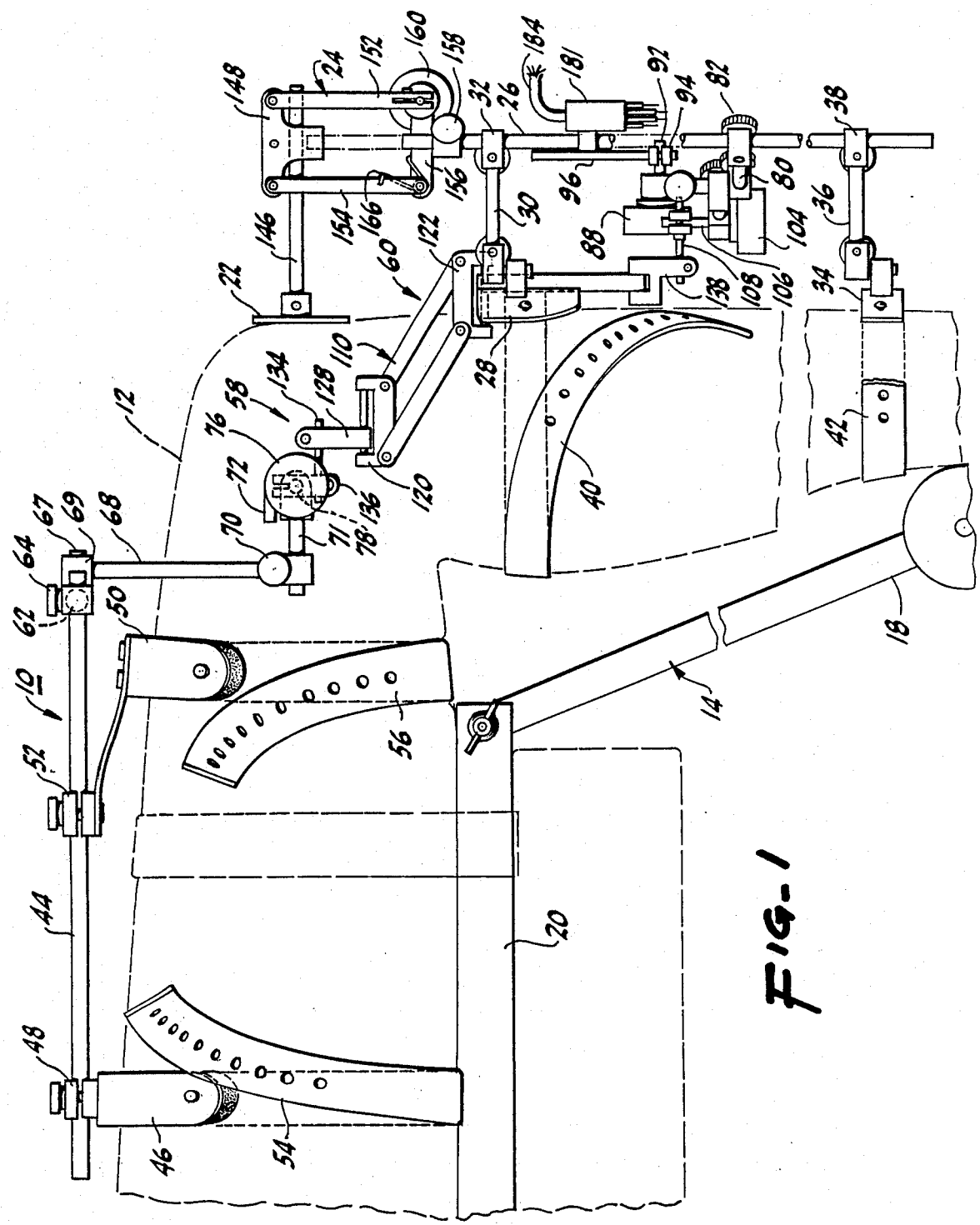
FIG. 1 is a side elevational view of the knee test apparatus installed on a patient seated on a leg support device.

Referring to FIG. 1 the dynamic knee test apparatus designated by the reference numeral 10 is shown mounted on a seated patient 12 shown in phantom. The patient's leg is supported on an adjustable leg support 14 as described in our referenced patent. The leg support 14 is employed in performing the traditional anterior/posterior force applications in full extension, 20° flexion flexion, as well as tibial rotation and varus-valgus moment angulation. Force is applied by hand or using a mechanical force applicator of the type described in the reference application or an applicator 6 of similar configuration shown in FIG. 8 having an electronic pressure sensitive transducer unit 17 for generating electrical signals corresponding to the value of force. The force applicator is primarily used for anterior/posterior tests. With the knee test apparatus strapped to the patient and the patient correspondingly strapped at his ankles to the extension 18 of the leg support 14 and at his thighs to the seat 20, force is applied below the knee to the front or back of the tibia. Deflections of the tibia relative to the femur are detected by a floating patella pad 22 which contacts the patella. The patella pad 22 is connected by a four bar parallelogram linkage assembly 24, shown in greater detail in FIGS. 6 and 7, to an elongated, light-weight, tibial rod 26 longitudinally positioned over the shin generally parallel to the axis of the tibia.

The tibial rod 26 is supported by an upper pad 28 and support post 30 slidably adjustable by screw clamp 32, and a lower pad 34 and support post 36, also slidably adjustable by a screw clamp 38. The upper pad 28 is positioned on the tibial tubercle, a stable location proximate the patella, and the strap 40 tightened. The lower pad 34 is positioned on the tibia at the lower shin above the ankle and the strap 42 tightened. The adjustments are to insure that the patella pad 22 is properly positioned against the center of the patella with the tibial rod support pads appropriately positioned on relatively stable bony prominances.

Similarly, a femoral rod 44 is supported by an upper pad 46 and adjustable support member 48 and a lower pad 50 adjustable and support member 52. Straps 54 and 56 retain the respective pads firmly against the patient's thigh. The femoral rod 44 is connected to the tibial rod 26 by a linkage assembly 58. Although the femoral rod 44 is fastened to the patient at relatively fleshy areas of the leg, the minimum friction generated by the linkage assembly eliminates detectable dislocations of the femoral rod during displacements of the tibial rod 26.

A spanning segment 60 of the linkage assembly 58 is arranged in two different configurations depending whether axial rotations of the tibial are to be measured, as shown in the assembly of FIGS. 1 and 2, or varus-valgus displacements are to be measured as shown in the partial assembly of FIG. 3. Referring to FIGS. 1 and 2, the femoral rod 44 has a perpendicular side post 62 connected to the end of the femoral rod 44 by screw clamp 64. The distal end of the side post 62 has a clamp 66 connecting a perpendicular junction peg 67. The junction peg 67 seats a vertical side post 68 with end clamps 69 and 70, the lower of which connects to a transducer post 71. The transducer post 71 has a collar clamp 72 which encircles the neck of the housing 74 of a flexion angle transducer 76 that senses axial motion by a projecting, rotatable transducer shaft 78. Adjustment of the angle of the side post 62 and its position on the femoral rod 44 will position the axis of the transducer shaft 78 proximate the pivot axis of the knee.

The tibial rod 26 also has a side post 80 with a screw clamp 82 for projecting the post perpendicular to the rod 26. The tibial post 80 is truncated to engage a cross post 84 in its end clamp 86. The cross post 84 has a varus-valgus transducer 88 clamped in a collar clamp 90 with its sensor shaft 92 clamped by a dual pin clamp 94 to an actuator lever 96 that is disengaged. Between the post clamp 86 and the transducer clamp 90 is an extension post clamp 98 and an extension post 100. In a screw clamp 102 at the distal end of the extension post 100 is an axial rotation transducer 104. The shaft 106 of the axial rotation transducer 104 has a cross pin clamp 107 on the shaft with a cross pin 108 to provide a crank arm for registering rotations of the tibial rod 26 relative to the femoral rod 44. In the arrangement of FIG. 2 the cross pin 108 is connected to the spanning segment 60, which in turn is connected to the flexion angle transducer 76. The spanning segment 60 is designed to permit displacement differentials, that is, variations in the distance between the axial transducer 104 and the flexion transducer 74 with minimal distortion in flexion angle measurements or axial rotation measurements since movement of the knee is not truly axial.

The spanning segment has a central parallel linkage unit 110 shown in greater detail in FIGS. 4 and 5. The parallel linkage unit 110 has a top link 112 and a pair of bottom links 114 connected to pivots 116 and 118 respectively in end brackets 120 and 122. The end brackets support pivotal shafts 124 and. 126 with connecting links 128 and 130 being fixed on the shafts but free to pivot with the shafts. Connecting link 128 has a clamp 132 that engages a crank pin 134 that is mounted perpendicular to the flexion transducer shaft 78 by a cross pin clamp 136, as shown in FIG. 1.

Connecting link 130 is a long extension with an end yoke link 138 pivotally connected in one alternative to the connecting link and clamped to the crank pin 108 of the rotational transducer shaft 106 by integral and clamp 139 as shown in FIGS. 1 and 2. Since the axial rotational transducer shaft is perpendicular to the flexion transducer shaft, the spanning segment 60 transmits flexion angle change to the flexion transducer 76 and axial rotation changes to the axial transducer 104. The third axis of angulation is absorbed the linkage.

Referring to the alternate connection arrangement of FIG. 3, the linkage assembly is oriented to detect varus-valgus displacements as well as flexion angulation. In FIG. 3 the spanning segment 60 is reoriented such that the clamp 132 of the connecting link 128 engages an elongated crank pin 140 connected to the flexion transducer shaft 78 by a cross pin clamp 142. The parallel link unit 110 shown on end has its connected extension link 130 directed toward the actuator lever 96 of the varus-valgus transducer 88. The yoke link 138 has its end clamp 139 clamped to the actuator lever 96. Angular side displacements of the leg using medial laxity procedures, are customarily accomplished by pushing with one hand on the outside of the knee while pulling with the other hand on the inside of the ankle or vice-versa. Medial-lateral knee displacements are instantly detected by angular rotation of the varus-valgus transducer shaft. Flexion angle is detected by the flexion transducer in the same manner as previously described.

Referring now to FIGS. 6 and 7 the linkage assembly 24 for detecting fore and aft displacements of the tibia relative to the femur is detailed. The floating patella pad 22 shown in FIGS. 1 and 2 is fastened to the end of a shaft 146. The patella shaft is slidable in a end mount 148 having a side split to accommodate a clamping screw 150 for securing the position of the shaft 146 and hence the patella pad 22 to the linkage assembly 24. The parallel links 152 and 154 have displaced pivotal connections to a transducer mount 156 at the other end. The transducer mount 156 is slidably clamped by clamp screw 158 to the end of the tibial rod 26, and supports an anterior/posterior laxity transducer 160. The axial shaft 162 of the transducer forms the pivot connection for the upper link 152 which is clamped by screw 163 to the shaft. The parallel linkage maintains the patella shaft in a substantially perpendicular orientation to the patella during fore and aft excursions of the tibia. Axial rotation of the transducer shaft 162 is calibrated to linear displacements of the patella pad relative to the tibial rod. The transducer is conveniently "zeroed" by extending the end of the rod 26 into a socket 164 in the end mount 148. The engaged position is also convenient for storage.

To insure that the pad 22 contacts the patella, a spring 166 on a pivot extension 168 for the lower link 154 engages the pivotal link 154 and stationary mount 156 to bias the linkage and hence the patella pad 22 against the patient's knee.

The four transducers are preferably highly sensitive potentiometers which, from a low voltage bus line, can develop a convenient low voltage analog signal for angular displacements. In the case of the anterior/posterior transducer the signal can be easily converted to represent linear displacements. These signals can be easily read by a simple volt meter for manual conversion, or a conventional signal processor for a more representative reading or record. The four electrical signal cables, 170, 172, 174 and 176 from the four transactions are combined in a junction box 178 mounted on the tibial rod 26 by a clamp bracket 180 as shown in FIG. 2. The junction box includes a multi-line socket 181 for a terminal plug 182 of a multi-line cable 184 leading to a signal processor.

Since it is preferred to apply measured force, particularly for the anterior/posterior tests, a force applicator 186 having an electrical signal output 188 is shown in FIG. 8. The electrical signal or signals are generated by the pressure sensitive transducers 190 within the casing 192 on the shank 194 of the applicator 186. The transducers respond to compression on pushing the contact pad 196 by the handle 198, as in pushing the shin, or to tension on pulling the contact pad 196 by the handle, as in pulling the calf. Since five signals are now available from the various transducers for application force, leg, flexion angle, anterior/posterior displacement, medial-lateral angulation, and tibial rotation, the signals are best processed and plotted by a small computer 200 by relatively simple programs after analog digital conversion by an A-D converter 202. Data can be stored and various plots can be made by output devices such as storage drives 204 and X-y plotters 206.

Using various inputs for ordinate and abscissa, a variety of useful graphic plots can be developed. In addition to the standard tests, the dynamic knee tester of this invention permits measurements while the patient stands with applied frontal anterior or lateral forces and even permits graphical plots to be taken of various laxities while the patient normally walks. Because of the vastly expanded capabilities of the present system, many valuable diagnostic tests have yet to be devised. However, it is clear that study of the kinematics of the knee will be substantially advanced through use of the subject apparatus.

While the foregoing embodiments of the present invention have been set forth in considerable detail for the purposes of making a complete disclosure of the invention, it may be apparent to those of skill in the art that numerous changes may be made in such detail without departing from the spirit and principles of the invention.

A typical computer program listing for generating useful data and plottings is filed in an appendix to this application. The listing is in microfiche form and consists of one sheet with seventy-eight frames.

What is claimed is:

1. A dynamic sagittal knee test apparatus for measuring knee laxities of a patient comprising:
   a. a first elongated rod element constructed and adapted to be secured to the anterior portion of a patient's thigh with the first element fixed in position relative to the thigh along the femur;

b. a second elongated rod element constructed and adapted to be secured to a patient's shin with a supporting part of the second element in contact with the tibial tubercle and with the second element fixed in position relative to the shin along the tibia;

c. a displaceable contact member connected to the second element and constructed and adapted to contact a patient's patella, the contact member having means to maintain the member in contact with the patella during anterior and posterior displacement so the tibial tubercle relative to the patella;

d. first measuring means connected to the contact member for measuring anterior and posterior displacement of the tibial tubercle relative to the patella on application of anterior or posterior forces on the patient's lower leg;

e. linkage means adapted to be located on the side of the patient s leg interconnecting the first element and the second element the linkage means including means for accommodating displacement differentials occasioned by non-axial motion of the patient's knee on the flexion; and, f. second measuring means connected to the linkage means and adapted to be located at the side of the knee for measuring the relative angle between the first element and the second element on flexion of the patient's leg.

2. The apparatus of claim 1 wherein the first and second measuring means are first and second electronic transducers which generate a signal analogous to displacements.

3. The apparatus of claim 2 wherein the second transducer has an axial sensing shaft and the interconnecting linkage means includes a four bar parallelogram linkage as accommodating means for translating knee motion on flexion to an axial rotation at the axial shaft of the transducer.

4. The apparatus of claim 2 wherein the first transducer has an axial sensing shaft and the displaceable contact member includes a four bar parallelogram linkage for translating relative linear displacement to an axial rotation at the axial shaft of the transducer.

5. The apparatus of claim 2 in combination with a signal processor for accepting signals form said first and second transducers for display or recording.

6. The apparatus of claim 5 wherein the signal processor comprises a programmed computer.

7. The apparatus of claim 1 in combination with a leg support adapted to support a seated patient at the posterior of the thigh and posterior of the ankle, the leg support having an adjustment means for providing a plurality of flexion angles for the leg of the seated patient.

8. The apparatus of claim 1 wherein the linkage means interconnecting the first element and the second element includes third measuring means for measuring the relative angle between the first element and the second element on rotation of the patient's tibia with the patient's femur maintained substantially immobile.

9. The apparatus of claim 8 wherein the third measuring means is an electronic transducer which generates a signal analogous to relative rotations of the tibia.

10. The apparatus of claim 9 in combination with a force applicator having a fourth measuring means for measuring applied force by the force applicator.

11. The apparatus of claim 10 having means for recording measurements of the force applicator simultaneously with the measurements of the first, second and third measuring means.

12. The apparatus of claim 11 wherein the first second, third and fourth measuring means comprise electronic transducer which generate electronic signals analogous to the positions or force measured, the signals being simultaneously processed by a signal processor for display or recording.

13. The apparatus of claim 8 having means for recording measurements by the first, second and third measuring means simultaneously.

14. The test apparatus of claim 1 wherein the linkage means interconnecting the first element and the second element includes medial-lateral measuring means for measuring the relative angle between the first element and the second element on lateral displacement of the patient, ankle with the patient's femur maintained substantially immobile.

15. The apparatus of claim 14 wherein the medial-lateral measuring means is an electronic transducer which generates a signal analogous to relative lateral angular displacements of the tibia relative to the femur.

16. The apparatus of claim 14 having means for recording measurements by the first, second, and medial-lateral measuring means simultaneously.

17. A dynamic sagittal knee test apparatus for measuring knee laxities in a leg of a patient comprising:

an exosketal articulating frame structure constructed with:

a first elongated, rod member to the anterior of the thigh of a patient in a substantially fixed position parallel to the femur;

a second elongated rod member having first and second pad members with means for fastening the second rod member to the patient's shin in a substantially fixed position parallel to the tibia;

interconnecting means adapted to be proximate the side of the patient's knee for interconnecting the first rod member and the second rod member with the first member articulatable relative to the second member upon movement of the patient's leg;

flexion angle measuring means in said interconnecting means for measuring the angle or articulation of said first member relative to said second member in a first plane generally coinciding with the plane of flexion of the patient's lower leg; and medial-lateral measuring means in said interconnecting means for measuring the angle of articulation of said first member relative to said second member in a second plane perpendicular to the said first plane generally coinciding with the plane of lateral varus-valgus angulation of the patient's lower leg in combination with means on said second member for measuring displacement of a patient's tibial tubercle relative to the patient's patella, said measuring means on said second member including a contact pad with means for maintaining the pad in contact with the patient's patella during anterior and posterior displacement of the patient's tibia.

18. The apparatus of claim 17 having further measuring means for measuring the angle of rotation of said second member relative to said first member on an axis generally parallel with the axis of the patient's tibia.

19. A dynamic sagittal knee test apparatus for measuring knee laxities of a patient comprising:
   a. a first element constructed and adapted to be secured to a patient's thigh;
   b. a second element constructed and adapted to be secured to a patient's shin with a supporting part of the second element in contact with the tibial tubercle;
   c. a displaceable contact member connected to the second element and constructed and adapted to contact a patient's patella, the contact member having means to maintain the member in contact with the patella during anterior and posterior displacements of the tibial tubercle relative to the patella;
   d. first measuring means connected to the contact member for measuring anterior and posterior displacements of the tibial tubercle relative to the patella;
   e. linkage means interconnecting the first element and the second element; and
   f. second measuring means connected to the linkage means for measuring the relative angle between the first element and the second element on flexion of the patient's leg; wherein the first and second measuring means are first and second electronic transducers which generate a signal analogous to displacements, and wherein the first transducer has an axial sensing shaft and the displaceable contact member includes a four bar parallelogram linkage for translating relative linear displacement to an axial rotation at the axial shaft of the transducer.

20. A dynamic sagittal knee test apparatus for measuring knee laxities of a patient comprising:
   a. a first element constructed and adapted to be secured to a patient's thigh;
   b. a second element constructed and adapted to be secured to a patient's shin with a supporting part of the second element in contact with the tibial tubercle;
   c. a displaceable contact member connected to the second element and constructed and adapted to contact a patient's patella, the contact member having means to maintain the member in contact with the patella during anterior and posterior displacements of the tibial tubercle relative to the patella;
   d. first measuring connected to the contact member for measuring anterior and posterior displacements of the tibial tubercle relative to the patella;
   e. linkage means interconnecting the first element and the second element; and,
   f. second measuring means connected to the linkage means for measuring the relative angle between the first element and the second element on flexion of the patient's leg; wherein the first and second measuring mean are first and second electronic transducers which generate a signal analogous to displacements and wherein the second transducer has an axial sensing shaft and the interconnecting linkage means includes a four bar parallelogram linkage for translating knee motion on flexion to an axial rotation at the axial shaft of the transducer.

* * * * *